(12) United States Patent
Lang

(10) Patent No.: US 7,503,225 B2
(45) Date of Patent: Mar. 17, 2009

(54) ULTRASONIC FLOW SENSOR HAVING A TRANSDUCER ARRAY AND REFLECTIVE SURFACE

(75) Inventor: Tobias Lang, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/593,143

(22) PCT Filed: Jan. 24, 2005

(86) PCT No.: PCT/EP2005/050287

§ 371 (c)(1),
(2), (4) Date: Jun. 26, 2007

(87) PCT Pub. No.: WO2005/090929

PCT Pub. Date: Sep. 29, 2005

(65) Prior Publication Data

US 2007/0261501 A1    Nov. 15, 2007

(30) Foreign Application Priority Data

Mar. 18, 2004  (DE)  .................. 10 2004 013 251

(51) Int. Cl.
*G01F 1/66* (2006.01)
(52) U.S. Cl. .................. 73/861.25; 73/861.27
(58) Field of Classification Search .. 73/861.25–861.31
See application file for complete search history.

(56) References Cited

U.S. PATENT DOCUMENTS

| | | | | |
|---|---|---|---|---|
| 4,281,550 A | * | 8/1981 | Erikson | .................. 73/626 |
| 4,484,478 A | | 11/1984 | Haerkoenen et al. | |
| 4,532,812 A | * | 8/1985 | Birchak | .................. 73/861.27 |
| RE34,566 E | * | 3/1994 | Ledley | .................. 600/443 |
| 5,426,678 A | * | 6/1995 | Terhune et al. | .................. 376/252 |
| 5,440,937 A | * | 8/1995 | Lynnworth et al. | .................. 73/861.29 |
| 5,540,230 A | * | 7/1996 | Vilkomerson | .................. 600/454 |
| 5,966,169 A | * | 10/1999 | Bullis | .................. 348/81 |
| 5,974,889 A | * | 11/1999 | Trantow | .................. 73/624 |
| 5,987,991 A | * | 11/1999 | Trantow et al. | .................. 73/624 |
| 6,029,518 A | * | 2/2000 | Oeftering | .................. 73/570.5 |

(Continued)

FOREIGN PATENT DOCUMENTS

DE    199 24 319    12/2000

(Continued)

OTHER PUBLICATIONS

Tooru et al., *Measurement of Velocity and Viscosity of Liquid Using Surface Acoustic Wave Delay Line*, Japanese Journal of Applied Physics, Publications Office, Tokyo, Japan, vol. 29, No. Suppl. 29 -1, Jan. 1990, pp. 140-143.

*Primary Examiner*—Harshad Patel
(74) *Attorney, Agent, or Firm*—Kenyon & Kenyon LLP

(57) ABSTRACT

An ultrasonic flow sensor is used in particular for measuring the volumetric or mass flow of a fluid in a pipe. The sensor includes at least one ultrasonic transducer which is capable of emitting and receiving ultrasonic signals. An ultrasonic flow sensor, having in particular a simple and cost-effective construction and which functions according to the principle of beam drift, includes an array of a plurality of ultrasonic transducers which is positioned on one side of the pipe, a reflective surface lying opposite the array on which the emitted ultrasonic signals are reflected, and a receiver electronic system which evaluates the ultrasonic signal received from the ultrasonic transducers.

11 Claims, 2 Drawing Sheets

U.S. PATENT DOCUMENTS

| | | |
|---|---|---|
| 6,584,860 B1 * | 7/2003 | Feller et al. ............... 73/861.25 |
| 7,178,408 B2 * | 2/2007 | Martin .................... 73/861.25 |
| 2002/0083771 A1 | 7/2002 | Khuri-Yakub et al. |
| 2006/0065055 A1 * | 3/2006 | Barshinger et al. ............ 73/609 |
| 2008/0028868 A1 * | 2/2008 | Konzelmann et al. .... 73/861.25 |

FOREIGN PATENT DOCUMENTS

| | | |
|---|---|---|
| EP | 1 348 954 | 10/2003 |
| WO | 03/091671 | 11/2003 |

\* cited by examiner

ULTRASONIC FLOW SENSOR HAVING A TRANSDUCER ARRAY AND REFLECTIVE SURFACE

FIELD OF THE INVENTION

The present invention relates to an ultrasonic flow sensor, in particular for measuring the volumetric or mass flow of a fluid.

BACKGROUND INFORMATION

Ultrasonic flow sensors are used in particular for measuring the volumetric flow or mass flow or the flow rate of a gaseous or liquid medium flowing through a pipe. A typical ultrasonic flow sensor includes two ultrasonic transducers in offset position in the direction of flow, the transducers generating ultrasonic signals and emitting them to the other ultrasonic transducer, which receives them. As a function of the emission direction, the ultrasonic signals are either accelerated or decelerated by the flow. The ultrasonic signals are therefore received by the two transducers after different propagation times. An analysis electronic system is finally able to calculate the desired measured value from the propagation time difference of the ultrasonic signal in the direction of flow and of the ultrasonic signal in the opposite direction.

Another type of ultrasonic flow sensor utilizes the effect of beam drift. Normally, this type includes two transducer arrays positioned opposite from one another on a pipe (series positioning of a plurality of transducers), one of which functions as an emitting array and the other as a receiving array. The emitting array sends an ultrasonic signal to the opposite receiving array where the signal is detected. If a fluid flows through the pipe at a flow rate v, the sound waves emitted transverse to the direction of flow are carried along by the flow and thus diverted in the direction of flow (beam drift). The structure of such an ultrasonic flow sensor having two transducer arrays is relatively expensive and complex.

SUMMARY OF THE INVENTION

It is therefore the object of the present invention to devise an ultrasonic flow sensor which functions according to the principle of beam drift, which has a simple structure and may be implemented in a substantially more cost-effective manner.

An essential aspect of the present invention is to implement an ultrasonic flow sensor having only a single transducer array and a reflective surface lying opposite from the array and to operate the flow sensor in such a way that the transducer array emits ultrasonic signals to the opposite reflective surface and again receives the reflected signals. The extent of beam drift is a measure of the flow rate of the flowing medium. An essential advantage of this flow sensor is that only a single transducer array is necessary and it is possible to manufacture such a sensor in a manner which is cost-effective in particular.

In this case, the term "transducer array" is understood in particular to be a series made up of a plurality of ultrasonic transducers, preferably situated directly adjacent to one another. The individual transducers are preferably positioned in alignment and generate, for example, flat or cylindrical ultrasonic waves. However, the transducer array may also be designed in such a way that spherical, ellipsoidal or otherwise curved wave fronts are generated.

The transducer array according to the present invention is preferably pulse operated. This means that the individual ultrasonic transducers of the transducer array are electrically excited by pulses and generate a corresponding ultrasonic signal which after its propagation time—which is essentially a function of the pipe diameter and the sound velocity in the fluid—is again received by the transducers.

The frequency of excitations per unit of time, i.e., the number of ultrasonic signals that pass through the measuring path simultaneously, is in principle freely selectable. In this connection, it must only be taken into consideration that conventional transducers are unable to emit and receive simultaneously and thus emitting and receiving may not coincide at one point in time.

The sensor may be operated according to a first operating mode, e.g., similar to the "sing-around" (Note: sing-around normally refers to the fact that the propagation time is measured) method, in which the reception of an ultrasonic signal at the transducer array triggers the generation of a new ultrasonic signal. As a result, the ultrasonic signals constantly move back and forth.

According to a second operating mode, an oscillator periodically triggers the generation of the ultrasonic signals in such a way that a new ultrasonic signal is always emitted after an ultrasonic signal is received.

According to a third operating mode, the transducer array is activated in such a way that it emits a sequence of a plurality of ultrasonic signals within a turnaround time (i.e., the time an ultrasonic signal would need to travel from the transducer array to the reflective surface and back). In this case, even before the first of the ultrasonic signals has again reached the transducer array, at least one additional signal is coupled into the measuring path. This makes it possible to substantially increase the number of measurements per unit of time and accordingly also increase the measuring accuracy, the measuring time compared to n single measurements being significantly shorter. The difference in time between the single ultrasonic signals of a sequence must be selected in such a way that a transducer is ready to receive, i.e., is not operating in emit mode when a reflected ultrasonic signal arrives at the transducer.

The ultrasonic flow sensor preferably includes an emission electronic system enabling the single ultrasonic transducers to be excited individually and independently of one another. This makes it possible to set the path differences of the individual signals emitted by the ultrasonic transducers in such a way that a global ultrasonic wave having a specifiable wave front arises through interference. It is thus possible, for example, to generate an essentially cylindrical or spherical wave front that is reflected on the opposite reflective surface and again impinges on the transducer array in a focused condition. In this case, the reflective surface may simply be a part of the inside wall of the pipe without the necessity of a special adaptation to the wall.

According to another embodiment of the present invention, the individual transducers of the transducer array are excited synchronously so that interference of the individual signals produces a wave having a flat wave front. In this case, the reflective surface is preferably curved in such a way that the flat wave is focused and impinges bundled on the transducer array. In order to impede the flow as little as possible, the reflective surface should moreover be designed in such a way that it offers little resistance to the flow and generates no turbulences. To this end, the reflective surface may, for example, be implemented as a bulge in the inside wall of the pipe.

According to another embodiment of the present invention, a screening device is provided on the side of the reflective surface which causes the portion of the ultrasonic signal that impinges on the screening device not to be reflected back to the transducer array or only in attenuated form. The screening device may, for example, be implemented in such a way that the ultrasonic signal impinging on it is absorbed, scattered or reflected out of the sound path of the useful signal. As a result, an intensity pattern is depicted on the transducer array, the boundaries of which are relatively sharp and may thus be readily detected.

The screening device may, for example, be an area of the inside wall surface, which is, for example, roughened or provided with fine grooves in order to scatter the ultrasonic signal diffusely. For flow reasons, the grooves are preferably aligned with the direction of flow.

The transducer array is preferably mounted flush with the inside wall of the pipe. As a result, the flow of the fluid is not disturbed and in particular no turbulences occur.

Furthermore, the transducer array according to the present invention is preferably mounted in the upper half of a pipe. This has the advantage that only a small amount of dust or suspended matter is able to collect at the transducer array. If the transducer array and the reflective surface are situated laterally opposite from one another on the pipe, both elements are subject to relatively little contamination.

Preferably, the ultrasonic flow sensor includes an emission and receiver electronic system which excites the transducer array in the desired manner and detects and evaluates the reflected ultrasonic signal.

DETAILED DESCRIPTION

Figure 1:
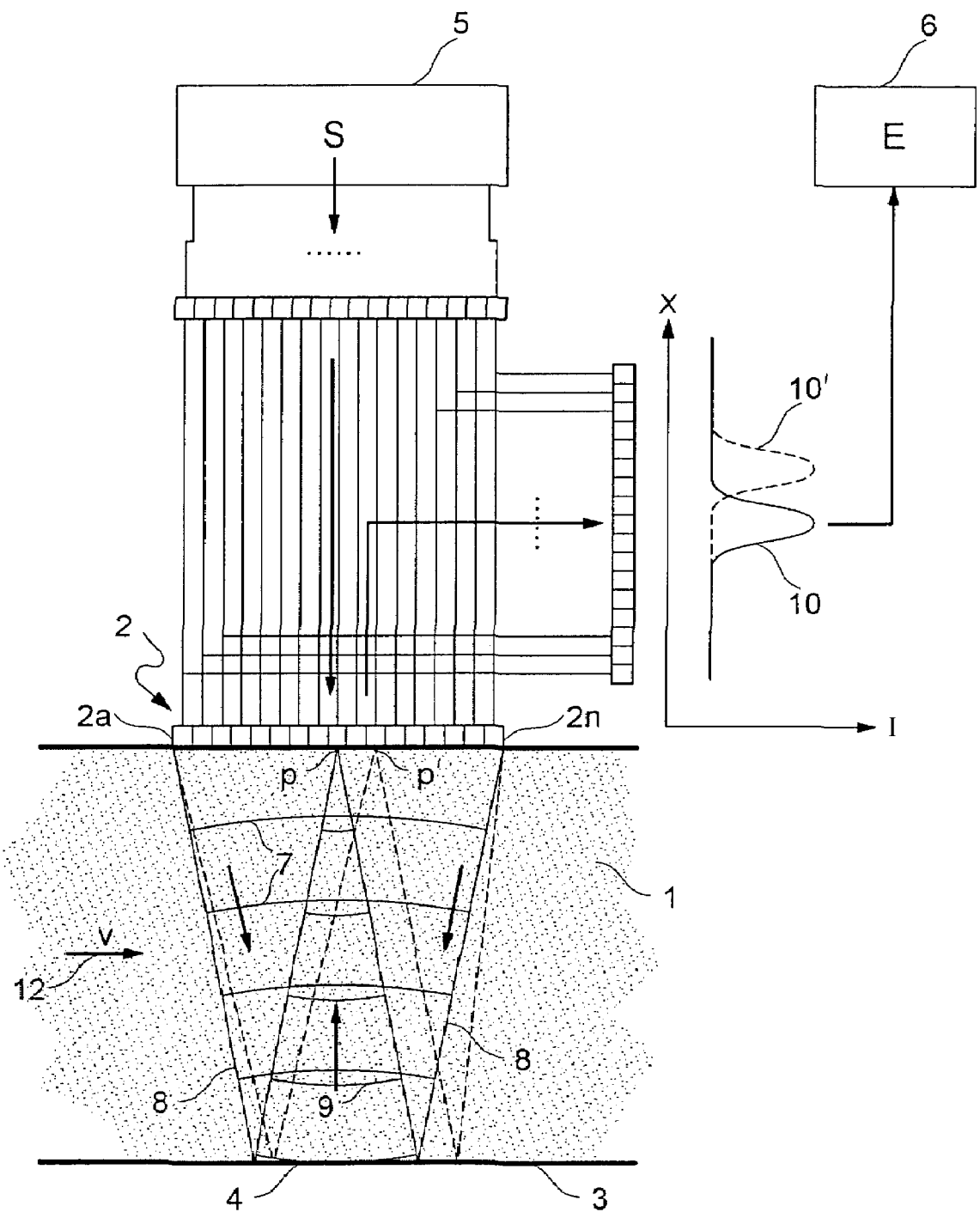
FIG. 1 shows a schematic view of an ultrasonic flow sensor according to a first embodiment of the present invention.

FIG. 1 shows an ultrasonic flow sensor for measuring the volumetric or mass flow of a fluid 1 flowing through a pipe 3. The flow sensor essentially includes an ultrasonic transducer array 2 of a plurality of individual ultrasonic transducers 2a through 2n in the form of parallel strips, each of which generates ultrasonic signals and emits them to a reflective surface 4 opposite to them. Interference of the individual signals produces a global wave front 7, which is propagated through flowing fluid 1 transverse to the direction of flow, is reflected on reflective surface 4 and again impinges on transducer array 2. The position of scanning point P is a measure of flow rate v of fluid 1.

In this exemplary embodiment, individual ultrasonic transducers 2a through 2n of transducer array 2 are activated separately, so that, due to the path differences of the individual signals, an approximately cylindrical wave front 7 curved concavely in the direction of flow arises, edge areas 8 of the wave front impinging on reflective surface 4 first. This focuses wave 7 and it impinges on transducer array 2 at point P in an essentially linear form. As a function of flow rate v, scanning point P moves more or less strongly in direction of flow 12 (effect of beam drift). The beam path at a higher flow rate v is denoted by dashed lines and a scanning point P'.

At the top right, FIG. 1 shows intensity distribution 10 or 10' of a received ultrasonic signal 9 at various flow rates v. At a low flow rate (or without flow), an intensity distribution 10 is produced at transducer array 2, the maximum of which is roughly in the center of transducer array 2. At a high flow rate, this maximum moves closer to the edge of transducer array 2. The associated intensity distribution of the sound intensity is denoted here by reference symbol 10'. A receiver electronic system 6 evaluates the ultrasonic signal detected at ultrasonic transducers 2a through 2n and calculates the desired measured value from it.

In this exemplary embodiment, reflective surface 4 is only a section of the inside wall of the pipe opposite transducer array 2. In order to improve the reflection properties, it would be possible, for example, to polish the inside wall of the pipe in the area of reflective surface 4 or provide it with a special reflective layer.

In this case, transducer array 2 is placed at the top of pipe 3 to prevent dust or suspended matter from collecting at the transducer array. As an alternative, it would also be possible to mount transducer array 2 on the side of pipe 3 so that the reflective wall area also lies to the side of pipe 3 and would consequently be less contaminated.

Figure 2:
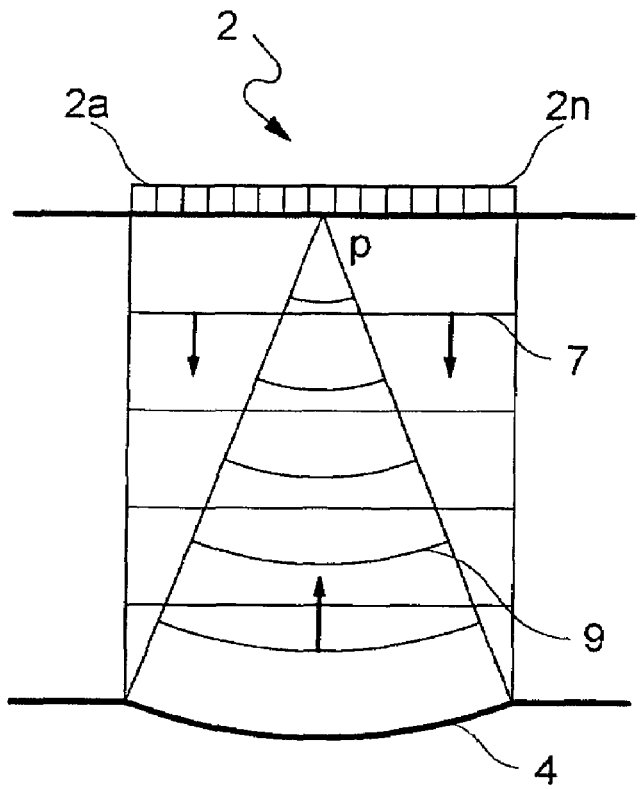
FIG. 2 shows a schematic view of an ultrasonic flow sensor according to a second embodiment of the present invention.

FIG. 2 shows a schematic representation of another embodiment of an ultrasonic flow sensor having a single transducer array 2 and an opposite reflective surface 4. Emission and evaluation circuits 5 and 6 have been omitted for the sake of clarity. Identical components are denoted by identical reference numerals.

In this exemplary embodiment, single ultrasonic transducers 2a through 2n of transducer array 2 are activated in such a way that interference of the individual signals causes a flat wave front 7 to be formed, which runs in the direction of reflective surface 4. Reflective surface 4 is curved in such a way that ultrasonic signal 9 is focused and impinges on transducer array 2 in an approximately linear or punctiform manner. Precise punctiform focusing is not absolutely necessary.

In the exemplary embodiment of FIG. 2, reflective surface 4 is designed as a bulge in the wall of pipe 3 in order not to impede the flow of fluid 1 and in particular to induce as little turbulence as possible.

Figure 3:
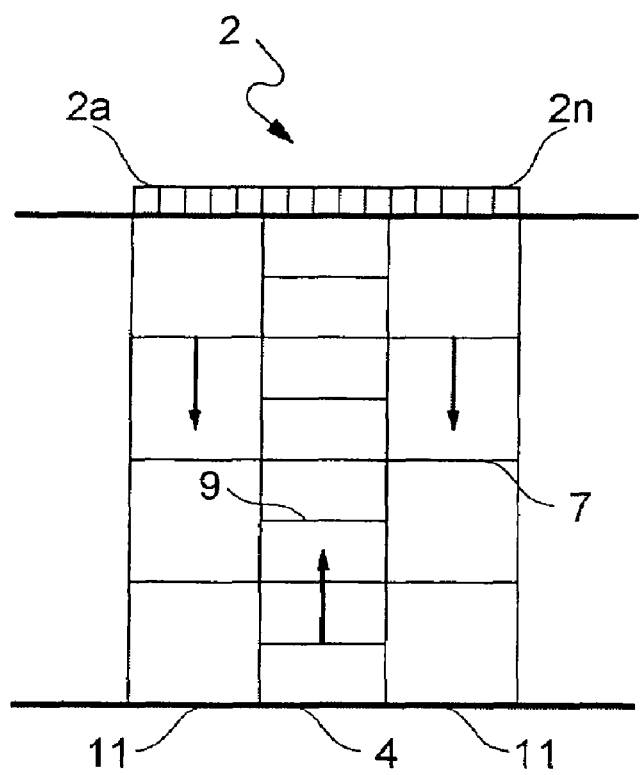
FIG. 3 shows a schematic view of an ultrasonic flow sensor according to a third embodiment of the present invention.

FIG. 3 shows another embodiment of an ultrasonic flow sensor having a single transducer array 2 and an opposite reflective surface 4. In this exemplary embodiment, the extension of reflective surface 4 is smaller than the length of transducer array 2. A screening device 11 is provided adjacent to reflective surface 4, the screening device attenuating or filtering the incident sound signal. This means that the portion of an ultrasonic signal 9 impinging on screening device 11 is not reflected back to transducer array 2 or is reflected back only in attenuated form. Screening device 11 may, for example, be implemented as a wall area having a surface which is rough in particular or, for example, as an area of the inside wall of the pipe provided with grooves.

A pattern having high sound intensity is thus produced at transducer array 2 caused by the part of signal 9 reflected on reflective surface 4 and one having low sound intensity is produced by the part of signal 9 attenuated at screening device 11. The boundaries of this pattern move in turn as a function of flow rate v of fluid 1. It is possible in turn to determine the desired measured value from the position of the pattern.

The invention claimed is:
1. An ultrasonic flow sensor, comprising:
    an array of a plurality of ultrasonic transducers for receiving and transmitting ultrasonic signals, the array being positioned on a pipe and emitting the ultrasonic signals to flow through a fluid flowing in the pipe;
    a reflective surface lying opposite the array; and
    a receiver electronic system that detects and evaluates an ultrasonic signal reflected on the reflective surface and received on the array;

wherein the transducers of the array are activated in such a way that a wave reflected on the reflective surface impinges on the array in one of an essentially punctiform manner and a linear manner.

2. The ultrasonic flow sensor as recited in claim 1, wherein the ultrasonic flow sensor is for measuring one of a volumetric flow and a mass flow of the fluid flowing in the pipe.

3. The ultrasonic flow sensor as recited in claim 1, wherein the array is pulse operated.

4. The ultrasonic flow sensor as recited in claim 1, further comprising:
   an emission electronic system for activating the individual ultrasonic transducers individually and independently of one another.

5. The ultrasonic flow sensor as recited in claim 4, wherein the individual ultrasonic transducers are operated in such a way that an ultrasonic wave is generated having an essentially cylindrical, spherical, ellipsoidal, or otherwise curved wave front.

6. The ultrasonic flow sensor as recited in claim 1, wherein the individual ultrasonic transducers are operated in such a way that an ultrasonic wave is generated having an essentially flat wave front.

7. The ultrasonic flow sensor as recited in claim 1, wherein the transducer array is mounted flush with an inside wall of the pipe.

8. The ultrasonic flow sensor as recited in claim 1, wherein the transducer array is mounted one of in an upper half and on a side of the pipe.

9. The ultrasonic flow sensor as recited in claim 1, wherein the reflective surface is a part of an inside wall of the pipe, a shape of the reflective surface not being modified in relation to other pipe sections.

10. The ultrasonic flow sensor as recited in claim 1, wherein the reflective surface is provided on a bulge of an inside wall of the pipe.

11. The ultrasonic flow sensor as recited in claim 1, further comprising:
    a screening device provided close to the reflective surface.

* * * * *